(12) United States Patent
Keret et al.

(10) Patent No.: US 12,409,567 B2
(45) Date of Patent: Sep. 9, 2025

(54) INTERCHANGEABLE END EFFECTOR AND STERILE BARRIER

(71) Applicant: Mazor Robotics Ltd., Caesarea (IL)

(72) Inventors: Amir Keret, Atlit (IL); Ziv Seemann, Beit Ytzhack (IL); Dvir Kadshai, Tel Aviv (IL); Ori Ben Zeev, Tel Aviv (IL); Itamar Eshel, Tzur Igal (IL); Gal Eshed, Atlit (IL); Dor Kopito, Kibbutz Parod (IL)

(73) Assignee: Mazor Robotics Ltd., Caesarea (IL)

( * ) Notice: Subject to any disclaimer, the term of this patent is extended or adjusted under 35 U.S.C. 154(b) by 907 days.

(21) Appl. No.: 17/357,647

(22) Filed: Jun. 24, 2021

(65) Prior Publication Data

US 2022/0409304 A1  Dec. 29, 2022

(51) Int. Cl.
| | | |
|---|---|---|
| *B25J 15/04* | (2006.01) | |
| *A61B 34/30* | (2016.01) | |
| *A61B 46/10* | (2016.01) | |
| *B25J 19/00* | (2006.01) | |
| *H01R 13/62* | (2006.01) | |
| *H01R 13/627* | (2006.01) | |
| *H01R 33/00* | (2006.01) | |

(52) U.S. Cl.
CPC .......... *B25J 15/0416* (2013.01); *A61B 34/30* (2016.02); *A61B 46/10* (2016.02); *B25J 19/0025* (2013.01); *B25J 19/0075* (2013.01); *H01R 13/6205* (2013.01); *H01R 13/6276* (2013.01); *H01R 33/00* (2013.01); *H01R 2201/12* (2013.01)

(58) Field of Classification Search
CPC .. B25J 15/0408; B25J 15/0416; B25J 15/045; B25J 15/0458; B25J 19/0025; B25J 19/0029; B25J 19/0033; B25J 19/0075; A61B 34/30; A61B 46/10; H01R 13/6205; H01R 13/6267; H01R 33/00; H01R 2201/22
See application file for complete search history.

(56) References Cited

U.S. PATENT DOCUMENTS

| | | |
|---|---|---|
| 7,350,373 B1 * | 4/2008 | Faries, Jr. .............. A61B 46/10 128/849 |
| 8,413,948 B2 | 4/2013 | Kemeny |
| 8,998,799 B2 | 4/2015 | Orban, III et al. |
| | | (Continued) |

OTHER PUBLICATIONS

Official Action for U.S. Appl. No. 17/357,640, dated Jun. 25, 2024 8 pages.

*Primary Examiner* — Joseph Brown
(74) *Attorney, Agent, or Firm* — Sheridan Ross P.C.

(57) ABSTRACT

Systems and methods for changing an end effector are provided. A connecting plate may have a first side, a second side opposite the first side, and a kinematic interface. The kinematic interface may include at least one projection extending from both the first side and the second side. A robot flange may have a first kinematic receiver including at least one recess for receiving a corresponding projection of the at least one projection of the first side. An end effector may have a second kinematic receiver and a locking assembly. The second kinematic receiver may include at least one recess for receiving a corresponding projection of the at least one projection of the second side. The locking assembly may be configured to releasably secure the end effector to the robot flange.

20 Claims, 11 Drawing Sheets

(56) References Cited

U.S. PATENT DOCUMENTS

| | | | |
|---|---|---|---|
| 10,357,324 B2 | 7/2019 | Flatt et al. | |
| 10,888,386 B2 | 1/2021 | Eyre et al. | |
| 2016/0058513 A1* | 3/2016 | Giorgi | A61B 46/10 |
| | | | 606/130 |
| 2018/0000472 A1* | 1/2018 | Beira | B25J 19/0075 |
| 2018/0056527 A1* | 3/2018 | Farritor | A61B 17/00234 |
| 2018/0125597 A1 | 5/2018 | Gogarty et al. | |
| 2020/0170724 A1* | 6/2020 | Flatt | A61B 34/70 |
| 2021/0339404 A1* | 11/2021 | Miyashita | B25J 15/0408 |
| 2021/0370498 A1* | 12/2021 | Kudo | B25J 15/045 |

* cited by examiner

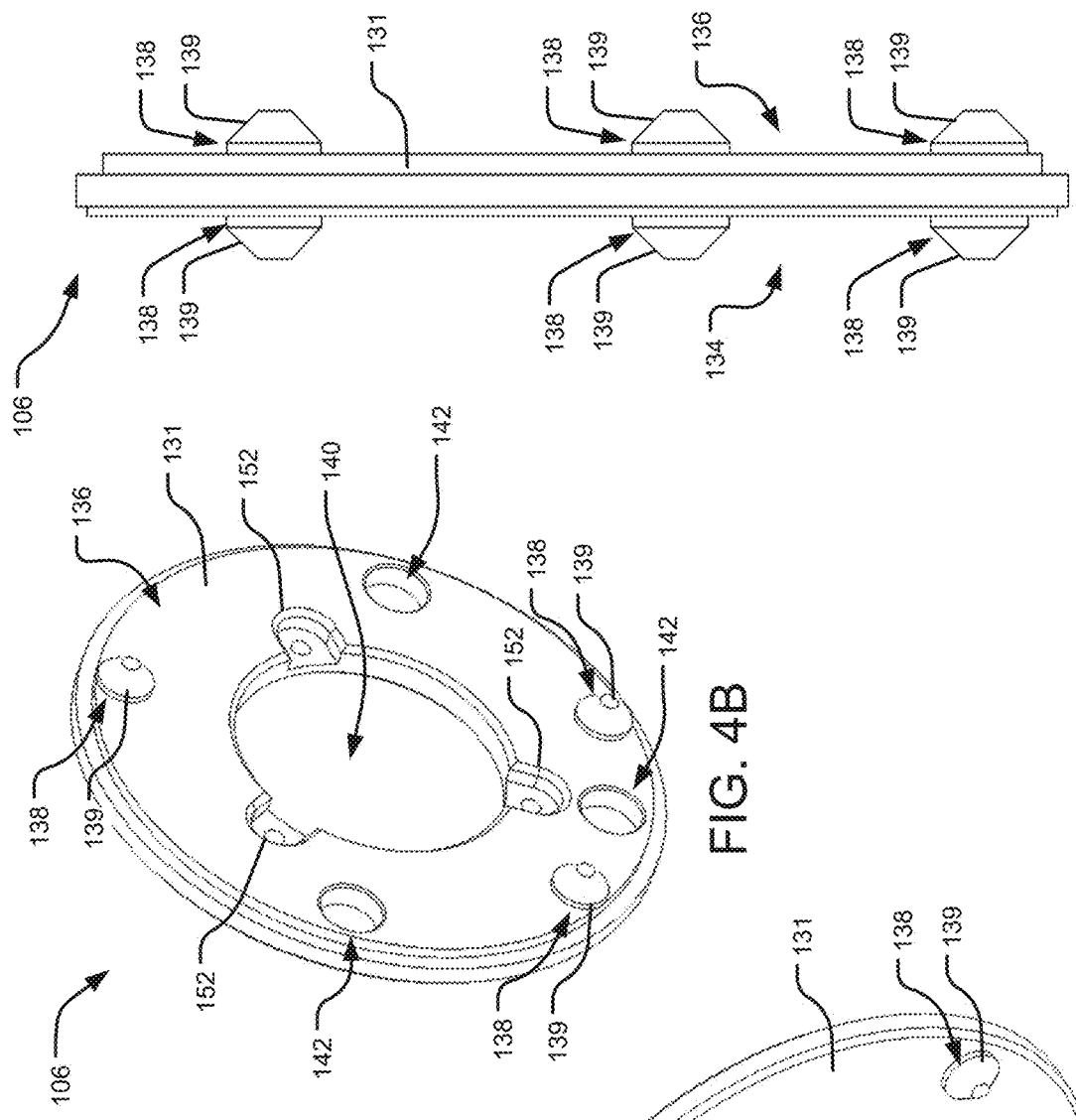
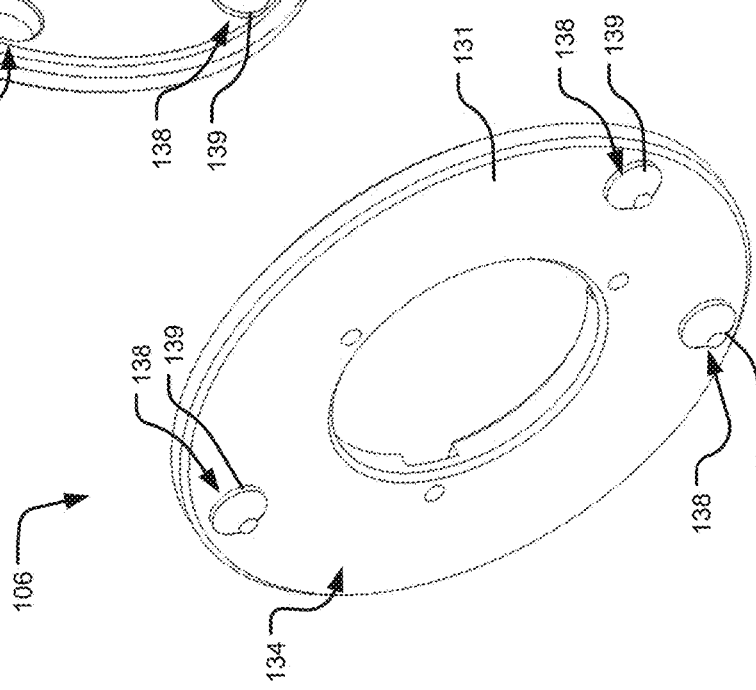

INTERCHANGEABLE END EFFECTOR AND STERILE BARRIER

FIELD

The present technology generally relates to an interchangeable end effector operable to be coupled to a robot, and relates more particularly to changing an end effector of a robot and delivering power and data from the robot to the end effector while maintaining a sterile barrier.

BACKGROUND

Various tools may be used during a surgical procedure and surgical robots may be used to assist a surgeon such procedures. The robots may support one or more tools. A sterile drape may also be used during a procedure to separate a sterile environment from a non-sterile environment.

SUMMARY

Example aspects of the present disclosure include:

A system for changing an end effector according to at least one embodiment of the present disclosure comprises a connecting plate having a first side, a second side opposite the first side, and a kinematic interface, the kinematic interface including at least one projection extending from both the first side and the second side; a robot flange having a first kinematic receiver, the first kinematic receiver including at least one recess for receiving a corresponding projection of the at least one projection of the first side; and an end effector having a second kinematic receiver and a locking assembly, the second kinematic receiver including at least one recess for receiving a corresponding projection of the at least one projection of the second side, the locking assembly configured to releasably secure the end effector to the robot flange, wherein the kinematic interface is received by the first kinematic receiver and the second kinematic receiver when the connecting ring is positioned between the robot flange.

Any of the aspects herein, wherein the connecting plate is circular.

Any of the aspects herein, wherein the at least one projection comprises at least one sphere.

Any of the aspects herein, wherein the at least one recess of each of the first kinematic receiver and the second kinematic receiver comprises a groove for receiving a corresponding sphere.

Any of the aspects herein, wherein the connecting plate is formed of a flexible material and the at least one sphere is formed of a rigid material.

Any of the aspects herein, further comprising a drape connectable to the connecting plate.

Any of the aspects herein, wherein the locking assembly also secures the drape to the robot flange when the end effector is secured to the robot flange by the locking assembly.

Any of the aspects herein, wherein the drape is integrated with the connecting plate.

Any of the aspects herein, wherein the end effector is configured to support a tool.

Any of the aspects herein, wherein the locking assembly comprises a set of projections disposed in a housing and a nut.

Any of the aspects herein, wherein the nut includes an angled surface disposed on an inner surface of the nut, the angled surface configured to move and compress each ball against the robot flange when the nut is tightened.

A system for changing an end effector according to at least one embodiment of the present disclosure comprises a robot flange having a first kinematic receiver and a first electrical connection, the first kinematic receiver including at least one recess for receiving a corresponding projection of the at least one projection of the first side; an end effector having a second kinematic receiver and a second electrical connection, the second kinematic receiver including at least one recess for receiving a corresponding projection of the at least one projection of the second side; and a connecting plate having a kinematic interface and an electrical connector, the kinematic interface including at least one projection, the electrical connector configured to transfer at least one of power and data from the first electrical connection to the second electrical connection, wherein the kinematic interface is received by the first kinematic receiver and the second kinematic receiver when the connecting ring is positioned between the robot flange.

Any of the aspects herein, wherein the first electrical connection comprises a spring pin connection.

Any of the aspects herein, wherein the robot flange comprises an aperture for supporting the first electrical connection, the end effector comprises an aperture for supporting the second electrical connection, and the connecting plate comprises an aperture for supporting the electrical connector.

Any of the aspects herein, wherein the at least one projection is integrated with the connecting plate.

Any of the aspects herein, wherein the at least one projection is rotatably within the connecting plate.

Any of the aspects herein, wherein the end effector supports a tool.

A system for changing an end effector according to at least one embodiment of the present disclosure comprises a robot flange having a first kinematic receiver and at least one magnet of a first polarity, the first kinematic receiver including at least one recess for receiving a corresponding projection of the at least one projection of the first side; an end effector configured to support a tool, the end effector having a second kinematic receiver, the second kinematic receiver including at least one recess for receiving a corresponding projection of the at least one projection of the second side; and a connecting plate having a kinematic interface and at leas tone magnet of a second polarity opposite the first polarity, the kinematic interface including at least one projection, wherein the kinematic interface is received by the first kinematic receiver and the second kinematic receiver when the connecting ring is positioned between the robot flange, and wherein the connecting plate is held in place against the robot flange when the at least one magnet of the first polarity is coupled to the at least one magnet of the second polarity.

Any of the aspects herein, further comprising a drape coupled to the connecting plate, the drape configured to cover at least the robot flange.

Any of the aspects herein, wherein a sterile barrier is formed when the drape covers the robot flange and the connecting plate is secured to the robot flange, the connecting plate being sterile.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 4A is a front isometric view of a connector to at least one embodiment of the present disclosure;

FIG. 4B is a rear isometric view of the connector of FIG. 4A;

FIG. 4C is a side view of the connector of FIG. 4A;

DETAILED DESCRIPTION

Figure 1:
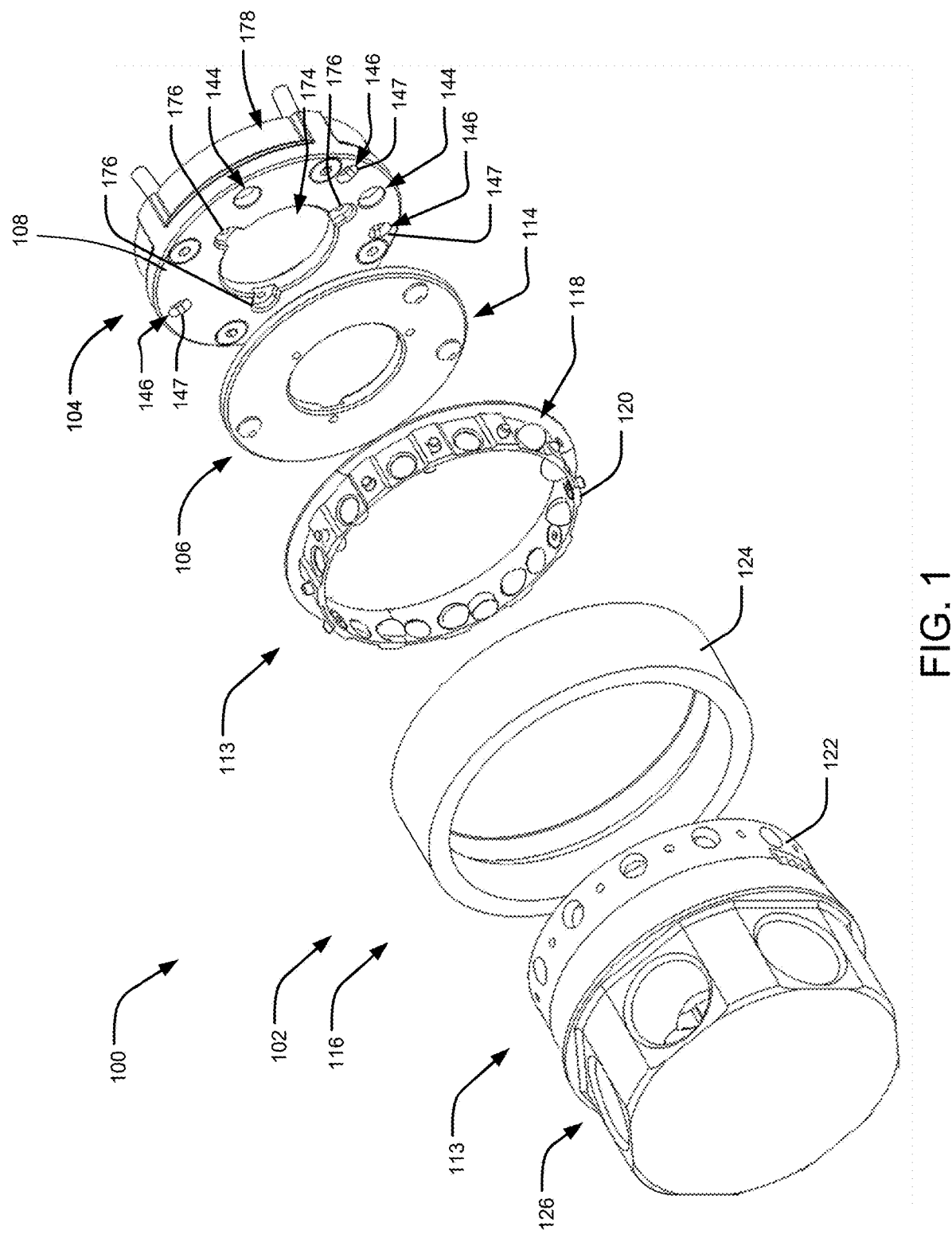
FIG. 1 is an isometric view of an interchangeable end effector system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

During a surgical procedure in an operating room, a patient may be kept within a sterile area in which the patient cannot be exposed to any object that is not sterile (e.g., a tool). Therefore, for example, a non-sterile robot may be covered in a drape (which may consist of, for example, a plastic bag). A challenge may exist where it is desirable to expose part of the non-sterile robot to the sterile area of the operating room in order to change an end effector or to transfer electricity to the sterile area from the robot. Thus, it is desirable to have a system and/or method to transfer electricity through the drape with a physical barrier and to change an end effector without exposing the non-sterile surgical robot to the sterile area.

At least one embodiment of the present disclosure allows for systems and methods for changing of various end effectors during a surgical procedure in the operating room without compromising the sterile area. The systems and methods provide a solution for robustly locking an end effector to a robot flange, drape integration, and transferring electronic supply, air supply, and/or communication to the end effector.

The system may include a robot "flange", which is the last component of the robot and is not sterile, fitted with a positioning interface, such as, for example, an accurate kinematic coupling interface, at its front and an angled surface around it. A connector, fixture, or fitting, such as, for example, a connecting ring or plate, fitted with the opposite side of the positioning interface, can connect to the robot flange. The connector may hold the drape (whether integrated with the drape or otherwise coupled to the drape) that covers the robot flange and, in some instances, the rest of the robot. The connector, in some embodiments, can be reprocessed and sterilized. The connector includes an electrical connector located in the middle of the ring that is used to transfer electric power and communications to the end effector and to seal a middle area of the ring. Thus, the robot flange is covered and is not exposed to the sterile area of the operating room.

The end effector is fitted with an opposite coupling interface to the connector that accurately positions itself and locks five degrees of freedom. The opposite coupling interface may, in some instances, be a coupling interface. The end effector may include a housing having holes containing spheres which are pushed against the robot flange as a nut closes. The drape may be between the spheres and the robot flange when the spheres are pushed against the robot flange. The systems and methods provide for: delivery of electric power and communication between a non-sterile environment to a sterile environment without breaking sterility; changing of end effectors without breaking sterility; peripheral locking to allow for the drape to be simple in design; an interface (which may be, in some instances, a kinematic interface) to provide for locking of five degrees of freedom; no part of the interface or the electrical connection is covered by the drape; a connector with electrical connectors that can be reprocessed; a connection plate with electrical connectors that are disposable; a drape that covers from the plate to the robot; an end effector having a locking assembly that comprises a housing, a nut, and 5 mm spheres that are, for example, standard stainless steel 440C; an end effector allowing a driver to be placed in the robot flange, therefore the robot flange may only receive 7 cables from a J6 connector and outputting 14 cables to the end effector; a driver that does not need to be reprocessed.

In some embodiments, an alternative connector or plate allows for the drape to come integrated with a kinematic interface. The kinematic interface of the connector may include three sphere bearing spheres and the kinematic interface of each of the end effector and the robot flange may have three corresponding grooves for receiving the spheres. In other embodiments, any kinematic interface or positional interface may be used. In embodiments with three spheres, the three sphere bearing spheres may be connected via a flexible structure that allows for deformation/wrinkles without tearing. In such embodiments, forces received by the end effector go through the spheres, but not the liner or drape. The flexible structure is used to keep a sterile barrier and hold the spheres roughly in place. The flexible structure can be made from plastic liner glued on the drape and the spheres. Touching surfaces of the kinematic interface that are not in contact with the liner may be an over mold of plastic, rubber, silicone, or formed from other flexible material. The drape can arrive with the kinematic interface (or any interface) already built in and allows for easy insertion in the operating room.

The alternative connector provides for a sterile barrier with multiple replacements during a procedure that is disposable, thereby removing the need to autoclave an item and lower its cost.

Embodiments of the present disclosure provide technical solutions to: (1) delivering power and/or data from a non-sterile environment to a sterile environment while maintaining a sterile barrier; (2) changing an end effector while maintaining a sterile barrier; (3) preventing forces from damaging a drape connected to an interface; and (4) increasing overall patient safety.

Turning first to FIG. 1, an isometric image of an interchangeable end effector system 100 is shown. The system 100 provides for an end effector 102 that can be removably coupled to a robot flange 104 of a robotic arm 112 (shown in FIG. 2) while maintaining a sterile boundary between the robotic arm 112 (which may not be sterile) and a sterile environment (such as, for example, a surgical site on a patient). The end effector 102 may be switched or changed with another end effector during, for example, a surgical procedure in which multiple tools may be used by the robotic arm 112.

The system 100 includes the end effector 102 connectable to the robotic flange 104 and a connector 106. In some embodiments, the connector 106 may be a connecting plate. In other embodiments, the connector 106 may be any type of fixture by which to connect and/or interface with the end effector 102 and/or the robotic flange 104. The connector 106 is disposed between the end effector 102 and the robot flange 104 when the end effector 102 is coupled to the robot flange 104. In some embodiments, the connector 106 may be sterilized and reused. In other embodiments, the connector 106 may be disposable.

Figure 7:
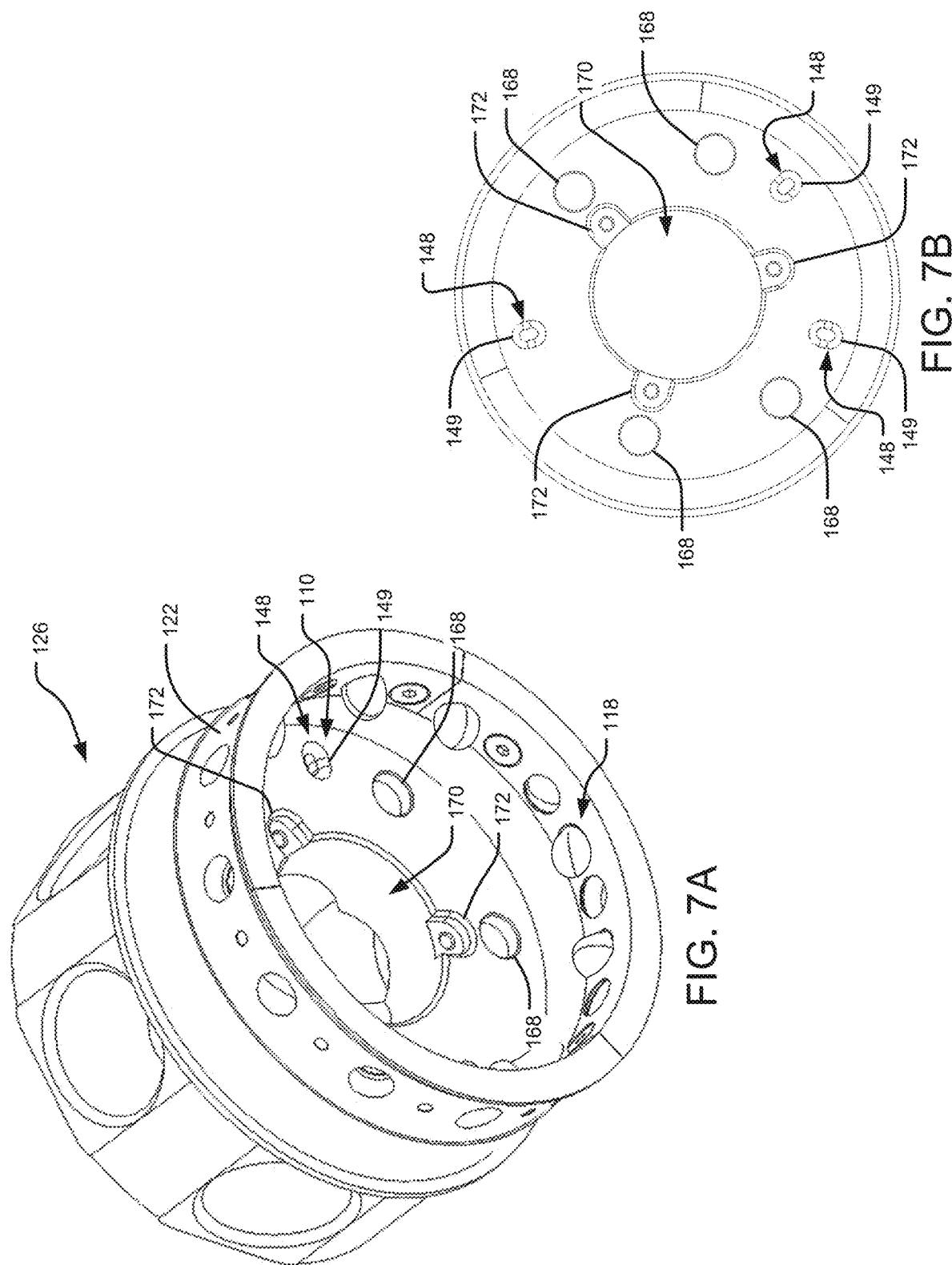
FIG. 7A is a bottom, tilted view of an end effector according to at least one embodiment of the present disclosure.
FIG. 7B is a bottom view of the end effector of FIG. 7A.

The robot flange 104 is positioned at an end 115 of the robotic arm 112 and includes a first receiver 108, which may be a first kinematic receiver. The end effector 102 includes a second receiver 110 (visible in FIGS. 7A and 7B), which may be a second kinematic receiver, and the connector 106 includes an interface 114, which may be a kinematic interface, that is receivable by the first receiver 108 and the second receiver 110. The first receiver 108 and the second receiver 110 may be any type of receiver and the interface 114 may be any kind of interface. The interface 114 and the first receiver 108 provide for alignment of the connector 106 to the robot flange 104 in a specific orientation and similarly, the interface 114 and the second receiver 110 provide for alignment of the connector 106 to the robot flange 104 in a specific orientation, as will be described in greater detail with respect to FIGS. 4 and 5.

The end effector 102 includes a base 126 configured to receive, support, and/or operate a tool or a component. The end effector 102 also includes a locking assembly 116 configured to releasably secure the end effector 102 to the robot flange 104. The locking assembly 116 includes a plurality of projections 118 disposed in a housing 113 and a nut 124. The housing 113 may comprise an inner ring 120 and an outer ring 122 and the plurality of projections 118 may be disposed between the inner ring 120 and the outer ring 122. The nut 124 is configured to compress the plurality of projections 118 against the robot flange 104 when the end effector 102 is secured to the robot flange 104. The end effector 102 and the locking assembly 116 will be described in greater detail with respect to FIGS. 7A-9.

Figure 2:
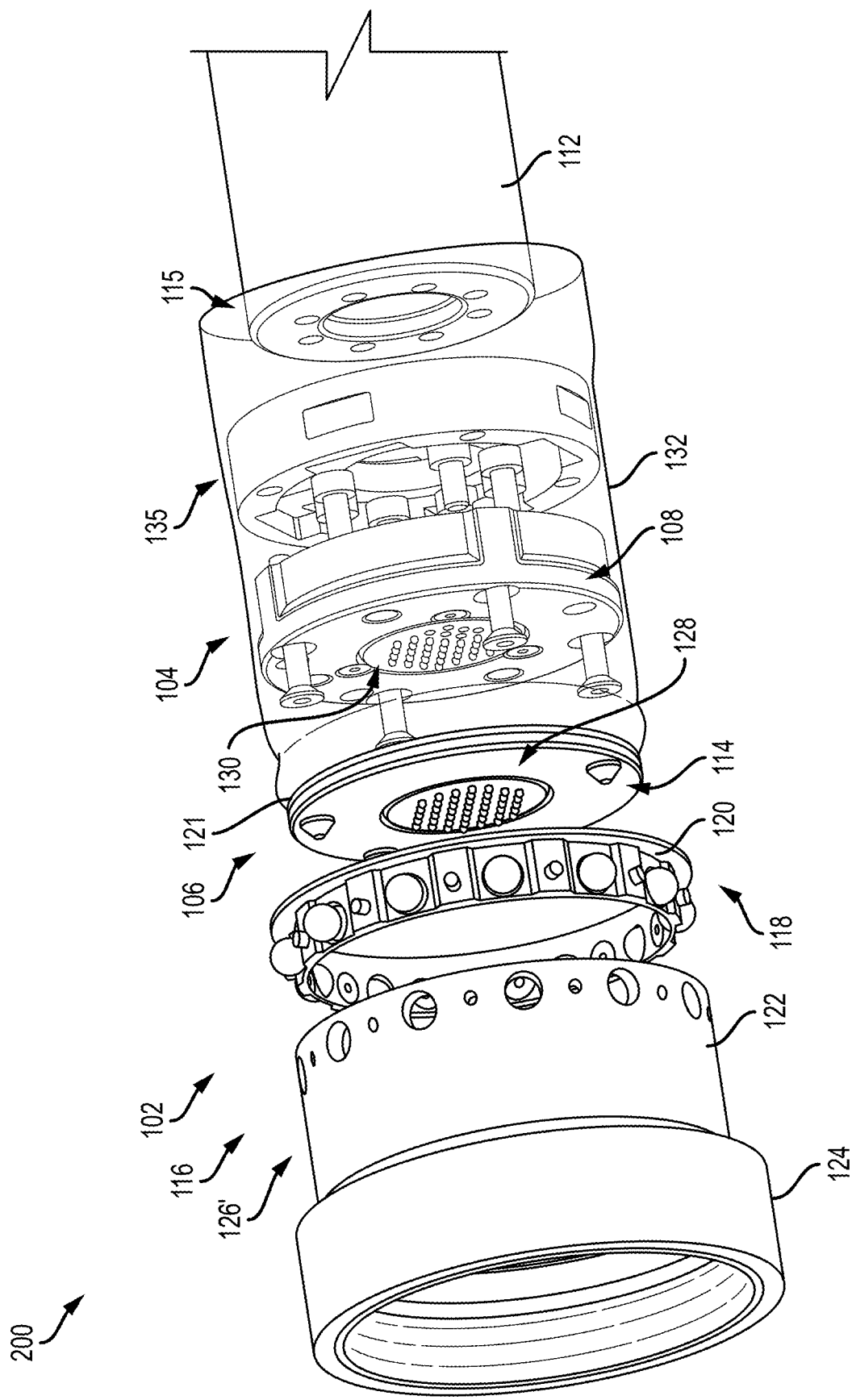
FIG. 2 is an exploded isometric view of an interchangeable end effector system and a robot flange according to at least one embodiment of the present disclosure.

The robot flange 104, as shown, includes an aperture 174. In embodiments where the robot flange 104 includes a first electrical connection 130 (such as shown in FIG. 2), the first electrical connection 130 may be received in the aperture 174. The robot flange 104 may also include at least one cut-out 176 adjacent to the aperture 174 for accommodating, for example, a screw head of a screw for securing the first electrical connection 130 to the robot flange 104.

Turning to FIG. 2, an isometric image of a system 200 is shown. The system 200 includes the same or similar components as system 100 and includes additional and/or alternative components. In the illustrated embodiment, the robot flange 104 is connected to the robot arm 112. In some embodiments, the robot flange 104 is connected to the robot arm 112 via a sensor 135 (which may be, for example, a force and torque sensor. In other embodiments, the robot flange 104 may be connected to the robot arm 112 directly. Also shown in the illustrated embodiment is an alternative base 126' of the end effector 102. It will be appreciated that the base 126' shown (as well as the base 126 shown in FIG. 1) is for illustrative purposes and that the base 126, 126' may have any form for receiving, supporting, and/or operating one or more tools or components.

Also shown in the illustrated embodiment, a drape 132 is coupled to the connector 106. The drape 132 is configured to cover at least the robot flange 104. In some embodiments, the drape 132 may cover the robotic arm 112. In other instances, the drape 132 may cover other components, instruments, and/or tools used during a surgical procedure. In some embodiments, the drape 132 may be coupled to the connector 106 by a ring 121 such as, for example, a snap ring, snapped over the drape 132 or an edge of the drape 132 and onto the connector 106. In some embodiments, the ring 121 may be snapped onto a groove of the connector 106. In other embodiments, the drape 132 may be adhered to the connector 106 using, for example, a glue. In some embodiments, the drape 132 may be releasable from the connector 106 and in some instances, disposed of. In some embodiments, the connector 106 may be sterilized for reuse. In other embodiments, the connector 106 may be disposed of. The drape 132 may be connected to the connector 106 during manufacture or assembly and shipped to an operating room as one piece. In other instances, the drape 132 may be shipped separate from the connector 106 to the operating room and the drape 132 and the connector 106 may be assembled together by a user, such as a medical provider or a surgeon, prior to a surgical procedure.

Figure 3:
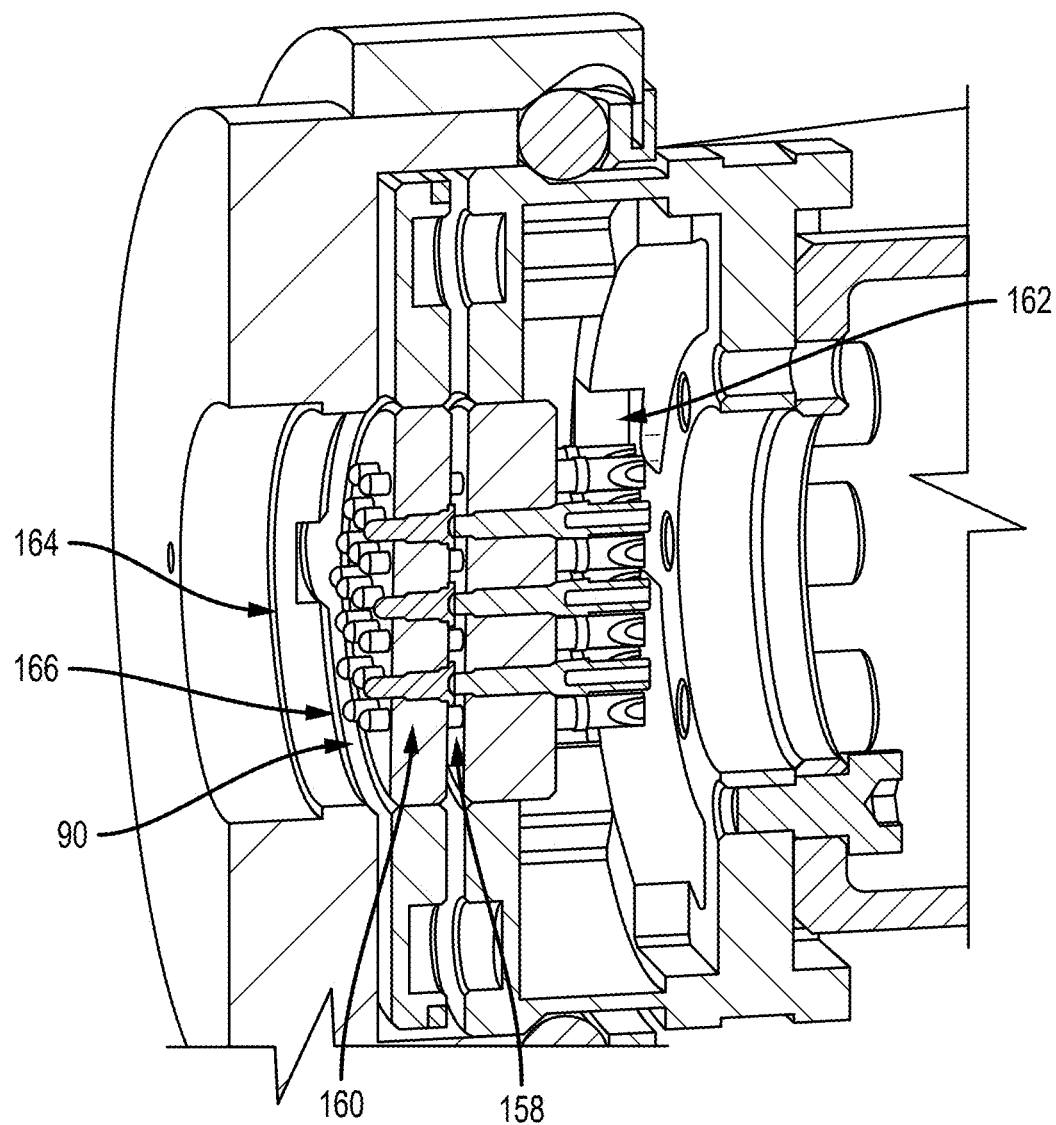
FIG. 3 is a cross-sectional side view of an interchangeable end effector system according to at least one embodiment of the present disclosure.

Turning to FIG. 3, a cross-section partial view of an assembled end effector 102, connector 106, and robot flange 104 is shown to illustrate an electrical connection between the connector 106 and the robot flange 104. In some embodiments, the robot flange 104 includes a first electrical connection 130, the end effector 102 includes a second electrical connection (not shown), and the connector 106 includes an electrical connector 128. The electrical connector 128 is configured to transfer at least one of power, ground, and/or data from the first electrical connection 130 to the second electrical connection when the end effector 102 is coupled to the robot flange 104. In some embodiments, the electrical connector 128 may be reprocessed for reuse. In other embodiments, the electrical connector 128 may be disposable. In some embodiments, the electrical connector 128 may be circular. In other embodiments, the electrical connector 128 may be any shape such as, for example, triangular, rectangular, square, or the like. In still other embodiments, the electrical connector 128 may be divided into separate segments.

In the illustrated embodiment, the first electrical connection 130 is a spring pin connection 162 (e.g., a pogo pin) having a plurality of male connectors 158 and the electrical connector 128 includes a spring pin connection 164 having a plurality of female connectors 160 for receiving the plurality of male connectors 158. The spring pin connection 164 of the electrical connector 128 may also include a plurality of male connectors 166 receivable by a plurality of female connectors (not shown) of the second electrical connection. Such electrical connection between the robot flange 104, the connector 106, and the end effector 102 provide for transferring of data and/or power from the robotic arm 112 to the end effector 102. In embodiments where the drape 132 is connected to the connector 106, data, ground, and/or power may be transferred from the robotic arm 112 to the end effector 102 while maintaining a sterile boundary between the robotic arm 112 (which may not be sterile) and the end effector 102 (which may be sterile). In some embodiments, the robot flange 104 may not include the first electrical connection 130, the end effector 102 may not include the second electrical connection, and/or the connector 106 may not include the electrical connector 128.

Turning to FIG. 4A to 4C, a front isometric view of the connector 106, a rear isometric view of the connector 106, and a side view of the connector 106 are respectively shown. As shown in the illustrated embodiment, the connector 106 is in the shape of a ring. In other embodiments, the connector may be any shape such as, for example a square, a triangle, or an oval. The connector 106 comprises a body 131 formed from any material. In some embodiments, the body 131 may be formed from, for example, metal, stainless steel, aluminum, or ceramic. In other embodiments, the body 131 may be formed from a flexible material such as, for example, plastic, rubber, or silicone. The connector 106 includes a first side 134, shown in FIG. 4A, and a second side 136, shown in FIG. 4B, opposite the first side 134. The connector 106 also includes an aperture 140. In embodiments where the connector 106 includes an electrical connector 128 (such as shown in FIG. 2), the electrical connector 128 may be received in the aperture 140. The connector 106 may also include at least one cut-out 152 adjacent to the aperture 140 for accommodating, for example, a screw head of a screw for securing the electrical connector 128 to the connector 106. The cut-out 152 may or may not extend completely through the body 131. In the illustrated example, the cut-out 152 extends partially, but not completely, through the body 131.

The interface 114 of the connector 106 includes at least one projection 138 extending from both the first side 134 and the second side 136, as shown in FIG. 4C. In some embodiments, shown in FIGS. 5 and 6, for example, the at least one projection 138 comprises a sphere. In other embodiments, such as the illustrated embodiment shown in FIG. 4C, the at least one projection 138 comprises a cone 139 disposed on each of the first side 134 and the second side 136. Also as shown in FIG. 4C, the at least one projection 138 may be integrated with the connector 106. In other embodiments, such as FIGS. 5 and 6, the at least one projection 138 may not be integrated with the connector 106. In the illustrated embodiment shown in FIGS. 4A-4C, the at least one projection 138 comprises three cones 139 on each of the first side 134 and the second side 136. It will be appreciated that in other embodiments, the at least one projection 138 may comprise fewer or greater than three cones 139 (or any shaped projection 138). In the illustrated embodiment, two cones 139 are spaced closer to each other than a third cone 139. In other embodiments, the three cones 139 may be spaced in any pattern or anywhere on the first side 134 or the second side 136. It will be appreciated that a first plurality of projections 138 may be disposed on the first side 134 in a pattern different from a pattern of a second plurality of projections 138 disposed on the second side 136. The spacing and/or pattern of the three cones 139 (or any shaped projection 138) may be a unique pattern such that the first receiver 114 and/or the second receiver 110 may only align with the interface 114 in a specific orientation.

Each projection 138 on the second side 136 may be received by, for example, at least one corresponding recess 146 of the first receiver 108 (shown in FIG. 2) disposed on a surface 150 of the robot flange 104. Similarly, each projection 138 on the first side 134 may be received by, for example, at least one corresponding recess 148 (shown in FIG. 7B) disposed on a surface 154 of the end effector 102. In the illustrated embodiment, each recess 146, 148 is a concavity 147, 149. In other embodiments, each recess 146, 148 may be any shape. The recess 146, 148 may have a diameter substantially the same as the at least one projection 138 or may have a diameter less or greater than the at least on projection 138. The recess 146, 148 may be sized and/or shaped to receive the at least one projection 138. In some embodiments, each recess 146, 148 may be the same size as each other, or may have a different size than each other.

In the illustrated embodiment, the connector 106 includes at least one magnet recess 142, each recess 142 receiving a magnet of a second polarity. As shown in FIGS. 1 and 2, the robot flange 104 includes a corresponding at least one magnet recess 144, each recess 142 receiving a magnet of a first polarity. The first polarity is opposite the second polarity. During assembly of the end effector 102, the robot flange 104, and the connector 106, the connector 106 may be held in place against the robot flange 104 when the at least one magnet of the first polarity is coupled to the at least one magnet of the second polarity. In other words, the connector 106 may be magnetically held in place on the robot flange 104. This provides for easy assembly of the end effector 102 onto the robot flange 104 without separately holding or supporting the connector 106 in place. In some embodiments, the connector 106 and/or the robot flange 104 may not include the at least one magnet recess 142, 144 or the magnet.

Figure 5:
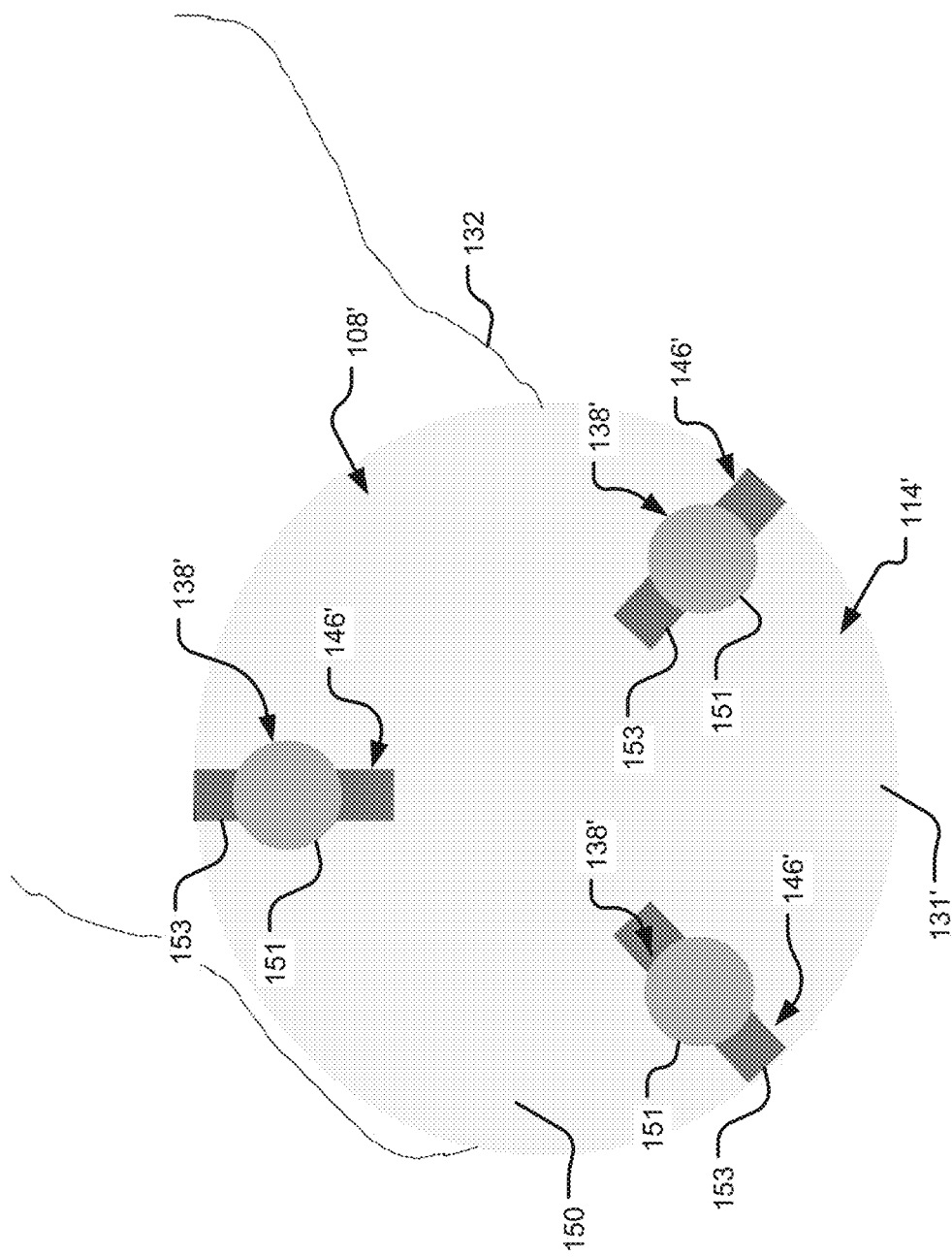
FIG. 5 is a schematic drawing of an interface according to at least one embodiment of the present disclosure.

Turning to FIG. 5, a schematic drawing of an alternative interface 108' of an alternative connector 106' and an alternative first receiver 108' is shown. In some embodiments, the alternative interface 108' may be a kinematic interface and the alternative first receiver 108' may be a first kinematic receiver. In some embodiments, the alternative connector 106' may a connecting plate. In other embodiments, the alternative connector 106' may be the same as or similar to the connector 106. The connector 106' includes a flexible body 131' connected to a drape 132. As previously described, the flexible body 131' may be integrated with the drape 132 in some embodiments. In other embodiments, the flexible body 131' may be a separate component from the drape 132 and coupled to drape 132. In some embodiments, the flexible body 131' may have a thickness greater than the drape 132. In other embodiments, the flexible body 131 may have the same thickness or a thickness less than the drape 132.

The interface 108' includes at least one projection 138' held in place or otherwise supported by the flexible body 131'. For example, the body 131' may include an aperture configured to receive a corresponding projection 138'. In some embodiments, the at least one projection 138' may be rigid and the flexible body 131' may be flexible. In the illustrated embodiment, the at least one projection 138' includes three spheres 151 and each sphere 151 may be rotatable in place. In other embodiments, the spheres 151 may be integrated with the body 131'. In other embodiments, the at least one projection 138' may include more or fewer than three spheres 151. In the illustrated embodiment, the body 131' is circular and the three spheres 151 are spaced equidistance around the body 131'. In other embodiments, the body 131' may be any shape and the three spheres 151 (or any number of projections 138') may be positioned anywhere on the body 131'. The spheres 151 may be formed from any material such as, for example, a metal, stainless steel, aluminum, or ceramic.

The first receiver 108' includes at least one recess 146' (visible through the body 131', which is shown as transparent in the illustrated embodiment) disposed on the surface 150 of the robot flange 104 for receiving a corresponding projection 138'. In the illustrated embodiment, each recess of the at least one recess 146' comprises a groove 153. In alternative embodiments, the at least one recess 146' may comprise a concavity or a recess of any shape. In As further illustrated, the at least one recess 146' comprises three grooves 153. In other embodiments, the at least one recess 146' may include more or fewer than three grooves 153. In the illustrated embodiment, the surface 150 is circular and the three grooves 153 are spaced equidistance around the surface 150. In other embodiments, the surface 150 may be any shape and the three grooves 153 (or any number of recesses 146') may be positioned anywhere on the surface 150.

Figure 6:
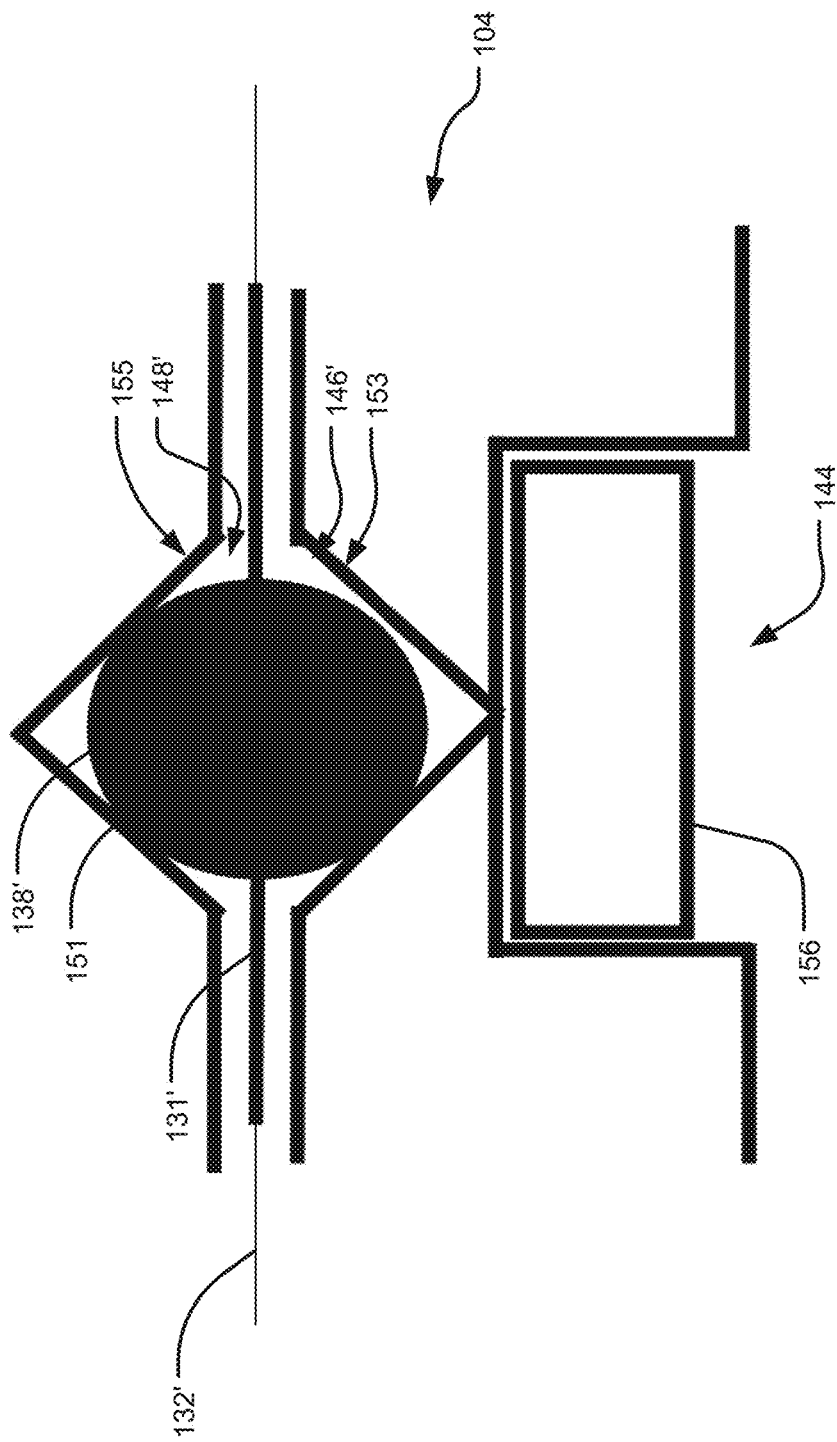
FIG. 6 is a schematic drawing of an interface according to at least one embodiment of the present disclosure.

Turning to FIG. 6, a side schematic view of a portion of the interface 114' and a drape 132', the first receiver 108' of the robot flange 104, and an alternative second receiver 110' of the end effector 102 are shown. In some embodiments, the second receiver 110' may be a second kinematic receiver. The interface 114' is connected to the drape 132', which may be the same as or similar to the drape 132. In the illustrated embodiment, the second receiver 110' is identical to the first receiver 108' and includes at least one recess 148' that comprises a groove 155. In alternative embodiments, the at least one recess 148' may comprise a concavity or a recess of any shape. In the illustrated embodiment, the robot flange 104 includes a magnet 156. The magnet 156 may be received in a recess 144 disposed on the surface 150 of the robot flange 104. In the illustrated embodiment, the recess 144 is positioned underneath the groove 153 so as to attract the sphere 151 (in embodiments where the sphere 151 is a metal such as, for example, steel) and thus, attract and hold the connector 106' in place against the robot flange 104. In other embodiments, the magnet may be positioned to attract a magnet of the opposite polarity positioned on the connector 106', as previously described.

As shown (and also visible in FIG. 5), each sphere 151 is received by a corresponding groove 153 of the first receiver 108' and a corresponding groove 155 of the second receiver 110'. In some embodiments, the spheres 151 may free to rotate until the end effector 102 is locked to the robot flange 104. In other embodiments, the spheres 151 may be integrated with the flexible body 131'. In such embodiments, the flexible body 131' allows for the spheres 151 to adjust or move into place in the corresponding grooves 153, 155. When the end effector 102 is being locked to the robot flange 104, the end effector 102 is linearly pulled towards to the robot flange 104, thereby pulling the second receiver 110' towards the first receiver 110'. During such motion, the groove 155 of the second receiver 110' and the groove 153 of the first receiver 108' are drawn together, thereby compressing the sphere 151 disposed between.

In some embodiments, when the second receiver 110', the first receiver 108', and the connector 106' are locked together, forces received by the end effector 102 are effectively transferred to the sphere 151. Because the forces received by the end effector 102 are transferred or directed to the sphere 151, the drape 132 experiences no force or less force than the sphere 151. Thus, the drape 132 is protected from large forces that may cause tearing or rupturing of the drape 132.

It will be appreciated that when the first receiver 108, 108', the second receiver 110, 110', and the interface 114, 114' are secured to each other, such securing locks five degrees of freedom (and the nut 124, or any locking mechanism, may lock a sixth degree of freedom). Further, as previously described, the interface 114, 114' and the first receiver 108, 108' also provide for alignment of the connector 106, 106' to the robot flange 104 and similarly, the interface 114, 114' and the second receiver 110, 110' provide for alignment of the connector 106, 106' to the robot flange 104.

Turning to FIG. 7A, a bottom isometric view of the base 126 of the end effector 102 is shown. The base 126, as shown, includes an aperture 170. In embodiments where the end effector 102 includes a second electrical connection, the second electrical connection may be received in the aperture 170. The base 126 may also include at least one cut-out 172 adjacent to the aperture 170 for accommodating, for example, a screw head of a screw for securing the second electrical connection to the base 126. In the illustrated embodiment, the base 126 includes at least one recess 168. The at least one recess 168 may receive at least one magnet. The at least one magnet may attract a magnet of the opposite polarity disposed in, for example, the connector 106 to align or orient the connector 106 to the end effector 102, or vice versa. It will be appreciated that the end effector 102 may not have the at least one recess 168 and/or the at least one magnet.

Turning to FIG. 7B, a bottom view of the base 126 is shown. As previously described, the base 126 includes at least one recess 148 for receiving a corresponding at least one projection 138. In the illustrated embodiment, each recess 148 is a concavity 149 shaped for receiving a corresponding cone 139. In the illustrated embodiment, the at least one recess 148 comprises three recesses 148. As shown, two of the recesses 148 are space closer to each other than a third recess 148. It will be appreciated that in other embodiments, the three recesses 148 may be shaped in any pattern or spacing.

Figure 8:
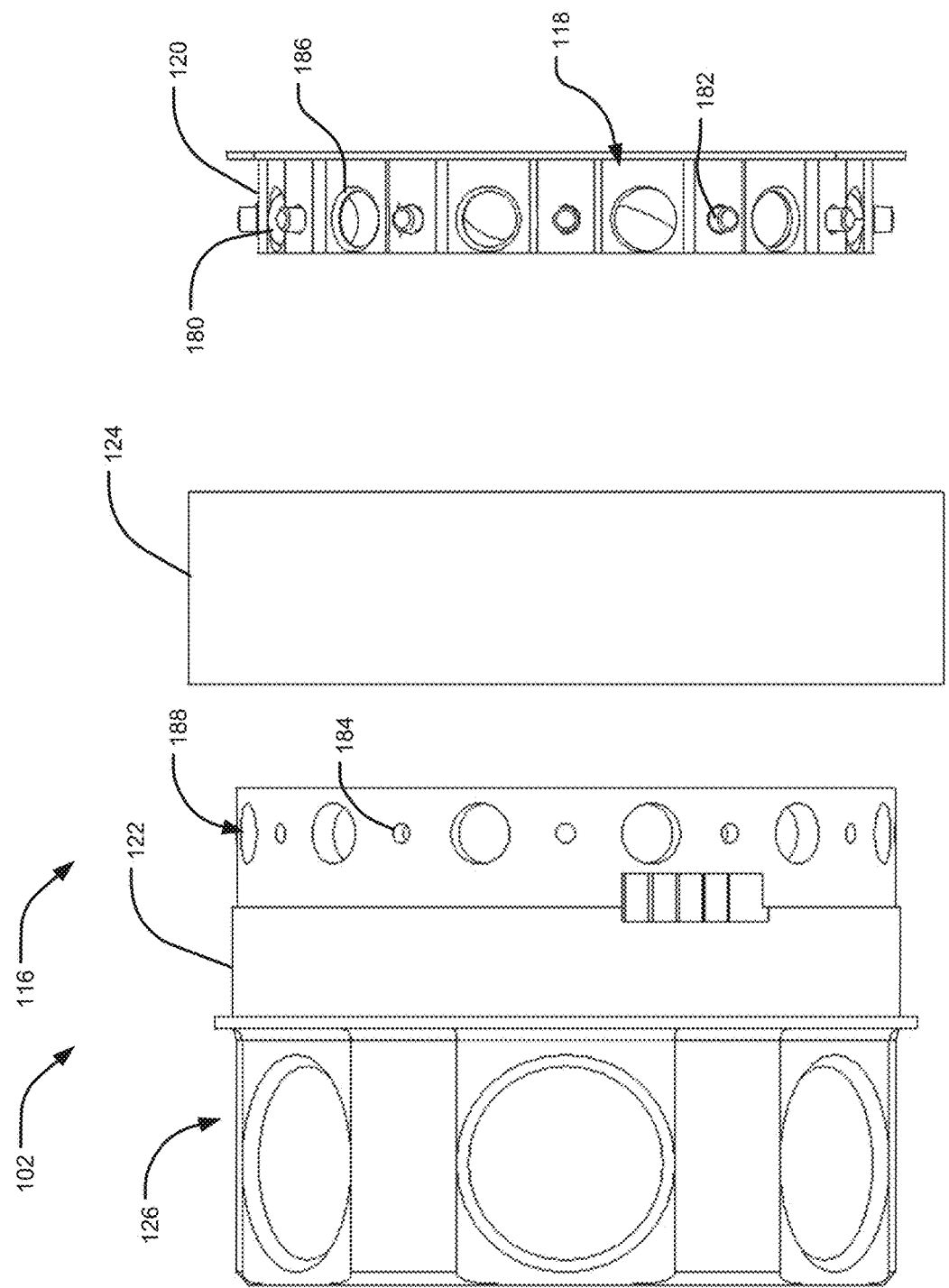
FIG. 8 is an exploded side view of an end effector according to at least one embodiment of the present disclosure.

Turning to FIG. 8, an exploded view of the end effector 102 is shown. Though not shown, the end effector 102 may be configured to support and/or operate a tool, an instrument, or any component such as, for example, an imaging device, a screwdriver, a screw, a rod, an ablation tool, or the like. The end effector 102 comprises the locking assembly 116, which is configured to releasably secure the end effector 102 to the robot flange 104. The locking assembly 116 allows for coupling of the end effector 102 to the robot flange 104 without damaging the drape 132 such that one or more end effectors may be switched and coupled to the robot flange 104 without damaging the drape 132.

The locking assembly 116 includes the plurality of projections 118 disposed in the housing 133. The housing 133 comprises the inner ring 120 and the outer ring 122. In some embodiments, the plurality of projections may be disposed between the inner ring 120 and the outer ring 122 along a periphery. The locking assembly 116 also includes the nut 124, which is configured to compress the plurality of projections 118 against the robot flange 104 when the nut 124 is secured to or tightened on the outer ring 122. In some embodiments each projection of the plurality of projections 118 may comprise a sphere 180. In some embodiments, the spheres 180 may have a diameter of 5 mm. In other embodiments, the spheres 180 may have a diameter less or greater than 5 mm. The spheres 180 may be formed from any material such as, for example, a metal, stainless steel, aluminum, or ceramic. As shown in the illustrated embodiment, the plurality of projections 118 are held in place on the inner ring 120 by the outer ring 122 secured to the inner ring 120 by a plurality of pins 182 secured in a set of corresponding apertures 184. As shown, the set of apertures 184 are disposed around a circumference of the outer ring 122 and the plurality of pins 182 are disposed around a circumference of the inner ring 120. The plurality of pins 182 may be secured in the set of apertures 184 by a press fit or by adhesion. In other embodiments, the outer ring 122 may be secured to the inner ring 120 by rivets, adhesion, screws, or the like.

The plurality of projections 118 are held in place between the inner ring 120 and the outer ring 122. More specifically and as shown in the illustrated embodiment, each of the inner ring 120 and the outer ring 122 includes a set of apertures 186, 188 (respectively) corresponding to the plurality of projections 118. Each aperture 186, 188 on the inner ring 120 and the outer ring 122 includes a diameter at least less than a diameter of a corresponding projection 118. In some embodiments, the diameter of each aperture 186, 188 on the inner ring 120 and the outer ring 122 are the same. In other embodiments, the diameter of each aperture 186, 188 on the inner ring 120 and the outer ring 122 are different. Each projection 118 is set between a corresponding aperture 186, 188 of the inner ring 120 and the outer ring 122 and held in place by each aperture 186, 188. Each projection 118 may also be rotatable in place between each aperture 186, 188 of the inner ring 120 and the outer ring 122, until at least the nut 124 is secured to the outer ring 122, in which each projection 118 will be compressed against the robot flange 104 and rotation is restricted.

The plurality of projections 118 disposed between the inner ring 120 and the outer ring 122 create a snap fit in which the end effector 102 may simply be snapped over the robot flange 104. The robot flange 104 may include one or more grooves 178 (shown in FIG. 2) that may receive the plurality of projections 118. The drape 132 may be positioned over the one or more grooves 178 such that when the end effector 102 is snapped over the robot flange 104, the drape 132 is also coupled to the robot flange 104. The one or more grooves 178 may comprise one groove extending around an entire circumference of the robot flange 104. In other instances, the one or more grooves 178 may comprise one groove extending partially around a circumference of the robot flange 104. In still other instances, the one or more grooves 178 may comprise a plurality of grooves disposed on the robot flange 104. During assembly, the end effector 102 may be coupled to the robot flange 104 via the snap fit between the plurality of projections 118 and the one or more grooves 178. The nut 124 may be used to lock the end effector 102 to the robot flange 104, as will be described in detail below.

Figure 9:
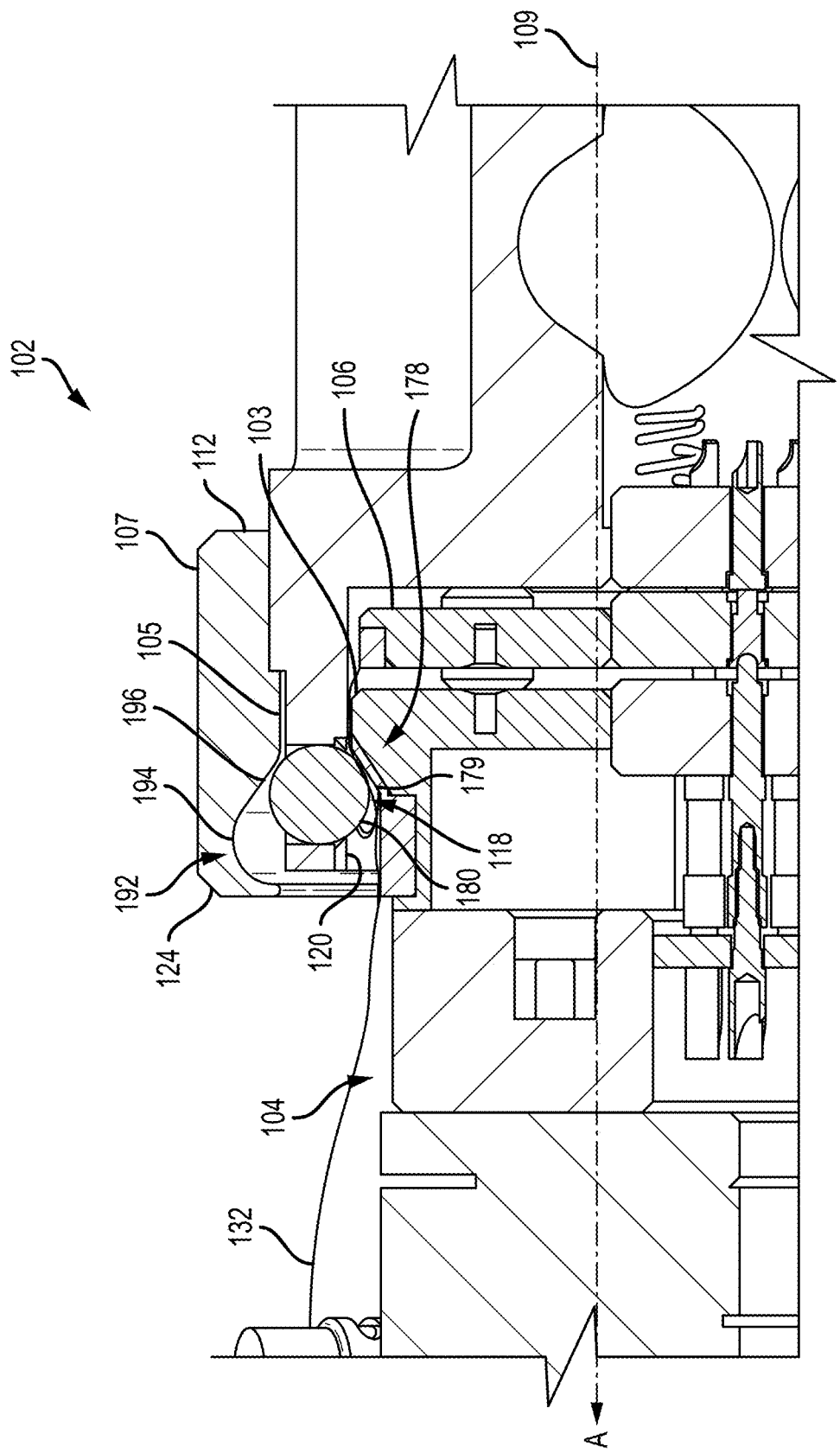
FIG. 9 is a partial cross-sectional side view of an interchangeable end effector system according to at least one embodiment of the present disclosure.

Turning to FIG. 9, the end effector 102 is shown in a locked state and locked to the robot flange 104. During assembly of the end effector 102 to the robot flange 104, the end effector 102 may be pushed onto the robot flange 104 until the plurality of projections 118 (and more specifically, for example, a plurality of spheres 180) snap over a lip 103 of the robot flange 104 and into the groove 178. As shown, the groove 178 may include an angled surface 179. It will be appreciated that in other embodiments, the groove 178 may comprise one planar surface, multiple planar surfaces, a rounded surface, or any number or shape of surfaces. In some embodiments, the snap fit may be provided by the plurality of projections 118 moving linearly within the inner ring 120 and the outer ring 122. In other embodiments, the snap fit may be provided by at least a portion of the inner ring 120 and/or the outer ring 122 comprising a flexible material and allowing for the inner ring 120 and/or the outer ring 122 to flex outwardly from a base position, stretch over the lip 103, then return to the base position when the projections 118 are disposed in the groove 178.

As previously described, the nut 124 is configured to lock the end effector 102 to the robot flange 104 by causing the plurality of projections 118 to compress against the grove 178. More specifically, in the illustrated embodiment, the nut 124 includes a locking recess 192 comprising a surface 196 that slopes from an inner surface 105 to a recess edge 194. The recess 192 may extend around an entire circumference of the inner surface 105. In other instances, the recess 192 may not extend around the entire circumference. In still other instances, the recess 192 may comprise a plurality of recesses disposed on the inner surface. The recess edge 194 is spaced between the inner surface 105 and an outer surface 107 of the nut 124. In the illustrated embodiment the recess edge 194 is rounded. In other embodiments, the recess edge 194 may be planar, angled, or any shape. The recess 192 is shaped so as to cause the spheres 180 to move and compress against the groove 178, thereby locking the end effector 102 to the robot flange 104. More specifically, when the nut 124 is initially positioned on the outer ring 122 and each sphere 180 is positioned in the recess 192, the sphere 180 may be within the recess 192 near the recess edge 194. As the nut 124 is moved onto the outer ring 122, the nut 124 moves linearly along an axis 109 in the direction of arrow A. As the nut 124 moves in the direction of A, the recess 192 also moves linearly in the direction of A, thus moving the surface 196 in the direction of A. As the surface 196 moves in the direction of A, the sloped angle of the surface pushes each sphere 180 against the groove 178 until the sphere 180 is compressed against the groove 178, thus locking the end effector 102 to the robot flange 104. In some embodiments, the nut may be rotated onto the outer ring via threads disposed on the inner surface 105 threading with threads disposed on an outer surface of the outer ring 122.

In embodiments where the connector 106 includes the drape 132, as shown, it will be appreciated that locking the end effector 102 to the robot flange 104 also secures the drape 132 to the robot flange 104. In other words, the locking assembly 116 also secures the drape 132 to the robot flange 104 when the locking assembly 116 secures the end effector 102 to the robot flange 104.

Figure 10:
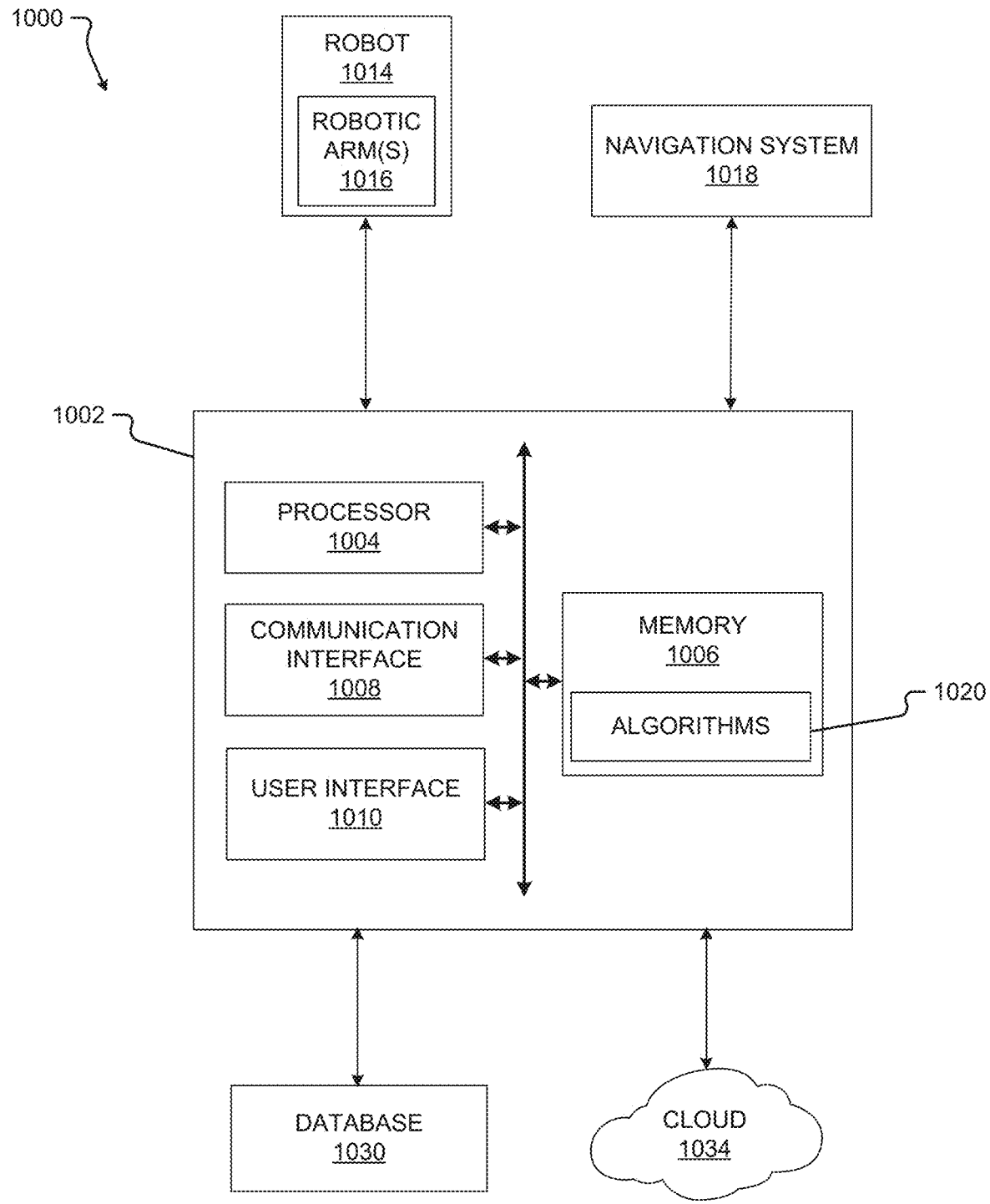
FIG. 10 is a block diagram of a system according to at least one embodiment of the present disclosure.

Turning to FIG. 10, a block diagram of a system 1000 according to at least one embodiment of the present disclosure is shown. The system 1000 may be used to change an end effector such as the end effector 102 using an interchangeable end effector system such as the system 100. The system may also be used to carry out one or more other aspects of one or more of the methods disclosed herein. The system 1000 comprises a computing device 1002, a robot 1014, a navigation system 1018, a database 1030, and/or a cloud or other network 1034. Systems according to other embodiments of the present disclosure may comprise more or fewer components than the system 1000. For example, the system 1000 may not include the robot 1014, the navigation system 1018, one or more components of the computing device 1002, the database 1030, and/or the cloud 1034.

The computing device 1002 comprises a processor 1004, a memory 1006, a communication interface 1008, and a user interface 1010. Computing devices according to other embodiments of the present disclosure may comprise more or fewer components than the computing device 1002.

The processor 1004 of the computing device 1002 may be any processor described herein or any similar processor. The processor 1004 may be configured to execute instructions stored in the memory 1006, which instructions may cause the processor 1004 to carry out one or more computing steps utilizing or based on data received from the robot 1014, the navigation system 1018, the database 1030, and/or the cloud 1034.

The memory 1006 may be or comprise RAM, DRAM, SDRAM, other solid-state memory, any memory described herein, or any other tangible, non-transitory memory for storing computer-readable data and/or instructions. The memory 1006 may store information or data useful for completing, for example, any step of the method 1100 described herein, or of any other methods. The memory 1006 may store, for example, one or more algorithms 1020. Such algorithms may, in some embodiments, be organized into one or more applications, modules, packages, layers, or engines. The algorithms may cause the processor 1004 to manipulate data stored in the memory 1006 and/or received from or via the robot 1014, the database 1030, and/or the cloud 1034.

The computing device 1002 may also comprise a communication interface 1008. The communication interface 1008 may be used for receiving image data or other information from an external source (such as the robot 1014, the navigation system 1018, the database 1030, the cloud 1034, and/or any other system or component not part of the system 1000), and/or for transmitting instructions, images, or other information to an external system or device (e.g., another computing device 1002, the robot 1014, the navigation system 1018, the database 1030, the cloud 1034, and/or any other system or component not part of the system 1000). The communication interface 1008 may comprise one or more wired interfaces (e.g., a USB port, an ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 1008 may be useful for enabling the device 1002 to communicate with one or more other processors 1004 or computing devices 1002, whether to reduce the time needed to accomplish a computing-intensive task or for any other reason.

The computing device 1002 may also comprise one or more user interfaces 1010. The user interface 1010 may be or comprise a keyboard, mouse, tracksphere, monitor, television, screen, touchscreen, and/or any other device for receiving information from a user and/or for providing information to a user. The user interface 1010 may be used, for example, to receive a user selection or other user input regarding any step of any method described herein. Notwithstanding the foregoing, any required input for any step of any method described herein may be generated automatically by the system 1000 (e.g., by the processor 1004 or another component of the system 1000) or received by the system 1000 from a source external to the system 1000. In some embodiments, the user interface 1010 may be useful to allow a surgeon or other user to modify instructions to be executed by the processor 1004 according to one or more embodiments of the present disclosure, and/or to modify or adjust a setting of other information displayed on the user interface 1010 or corresponding thereto.

Although the user interface 1010 is shown as part of the computing device 1002, in some embodiments, the computing device 1002 may utilize a user interface 1010 that is housed separately from one or more remaining components of the computing device 1002. In some embodiments, the user interface 1010 may be located proximate one or more other components of the computing device 1002, while in other embodiments, the user interface 1010 may be located remotely from one or more other components of the computer device 1002.

The robot 1014 may be any surgical robot or surgical robotic system. The robot 1014 may be or comprise, for example, the Mazor X™ Stealth Edition robotic guidance system. The robot 1014 may be configured to position a component, such as the end effector 102, at one or more precise position(s) and orientation(s), and/or to return the component to the same position(s) and orientation(s) at a later point in time. The robot 1014 may additionally or alternatively be configured to manipulate an end effector such as the end effector 102 (whether based on guidance from the navigation system 1018 or not) to accomplish or to assist with a surgical task. In some embodiments, the robot 1014 may be configured to hold and/or manipulate an anatomical element during or in connection with a surgical procedure. The robot 1014 may comprise one or more robotic arms 1016. The robotic arms 1016 may be the same as or similar to the robotic arm 112. In some embodiments, the robotic arm 1016 may comprise a first robotic arm and a second robotic arm, though the robot 1014 may comprise more than two robotic arms. Each robotic arm 1016 may be positionable independently of the other robotic arm. The robotic arms may be controlled in a single, shared coordinate space, or in separate coordinate spaces.

The robot 1014, together with the robotic arm 1016, may have, for example, one, two, three, four, five, six, seven, or more degrees of freedom. Further, the robotic arm 1016 may be positioned or positionable in any pose, plane, and/or focal point. The pose includes a position and an orientation. As a result, a surgical tool or other object held by the robot 1014 (or, more specifically, by the robotic arm 1016) may be precisely positionable in one or more needed and specific positions and orientations.

The robotic arm(s) 1016 may comprise one or more sensors that enable the processor 1004 (or a processor of the robot 1014) to determine a precise pose in space of the robotic arm (as well as any object or element held by or secured to the robotic arm).

In some embodiments, reference markers (i.e., navigation markers) may be placed on the robot 1014 (including, e.g., on the robotic arm 1016), or any other object in the surgical space. The reference markers may be tracked by the navigation system 1018, and the results of the tracking may be used by the robot 1014 and/or by an operator of the system 1000 or any component thereof. In some embodiments, the navigation system 1018 can be used to track other components of the system the system can operate without the use of the robot 1014 (e.g., with the surgeon manually manipulating one or more surgical tools based on information and/or instructions generated by the navigation system 1018, for example).

The navigation system 1018 may provide navigation for a surgeon and/or a surgical robot during an operation. The navigation system 1018 may be any now-known or future-developed navigation system, including, for example, the Medtronic StealthStation™ S8 surgical navigation system or any successor thereof. The navigation system 1018 may include one or more cameras or other sensor(s) for tracking one or more reference markers, navigated trackers, or other objects within the operating room or other room in which some or all of the system 1000 is located. The one or more cameras may be optical cameras, infrared cameras, or other cameras. In some embodiments, the navigation system may comprise one or more electromagnetic sensors. In various embodiments, the navigation system 1018 may be used to track a position and orientation (i.e., pose) of the robot 1014 and/or robotic arm 1016, and/or one or more surgical tools (or, more particularly, to track a pose of a navigated tracker attached, directly or indirectly, in fixed relation to the one or more of the foregoing). The navigation system 1018 may include a display for displaying one or more images from an external source (e.g., the computing device 1002 or other source) or for displaying an image and/or video stream from the one or more cameras or other sensors of the navigation system 1018. In some embodiments, the system 1000 can operate without the use of the navigation system 1018. The navigation system 1018 may be configured to provide guidance to a surgeon or other user of the system 1000 or a component thereof, to the robot 1014, or to any other element of the system 1000 regarding, for example, a pose of one or more anatomical elements, whether or not a tool is in the proper trajectory, and/or how to move a tool into the proper trajectory to carry out a surgical task according to a preoperative or other surgical plan.

The system 1000 or similar systems may be used, for example, to carry out one or more aspects of any of the method 1100 described herein. The system 1000 or similar systems may also be used for other purposes.

Figure 11:
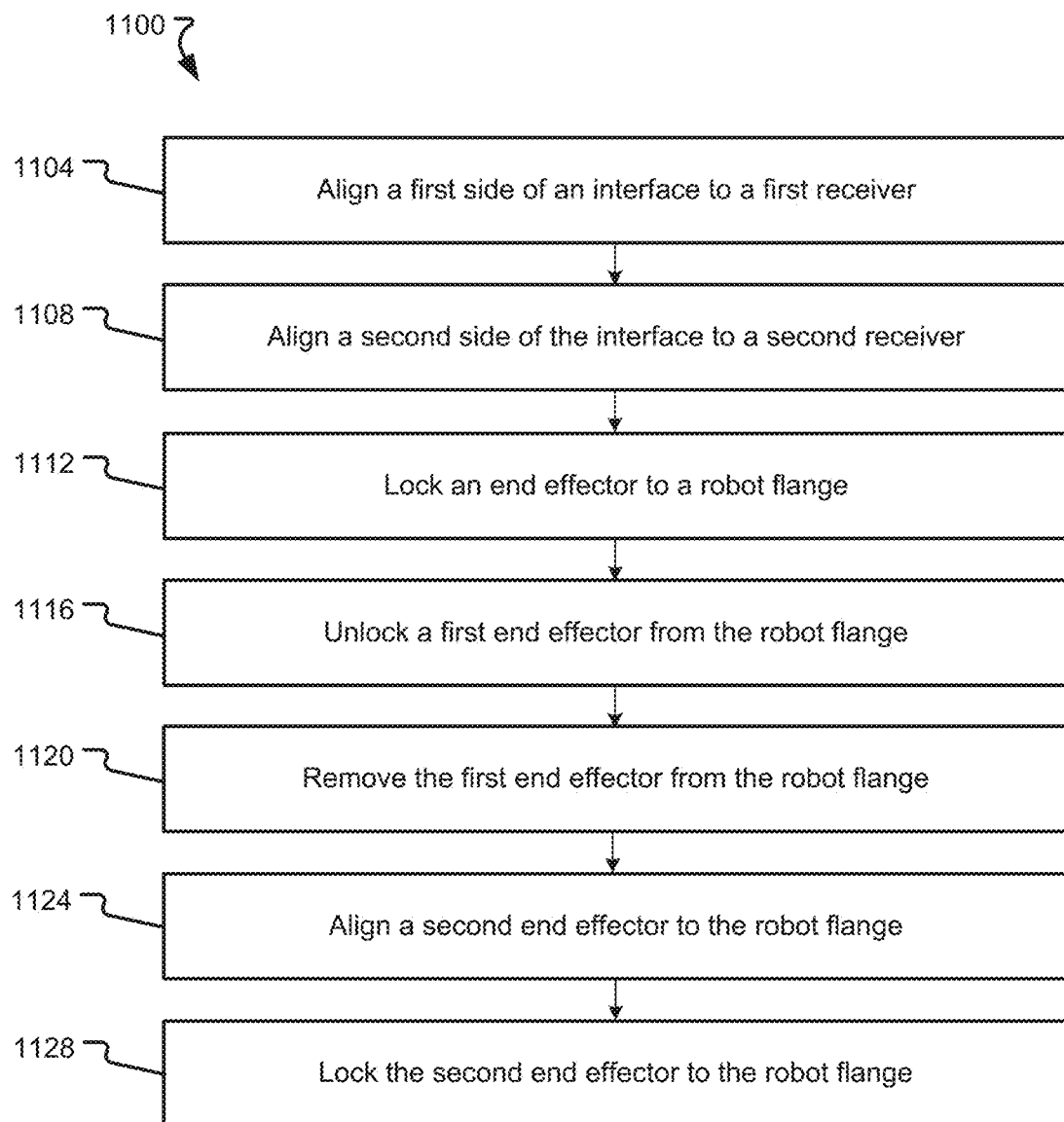
FIG. 11 is a flowchart according to at least one embodiment of the present disclosure.

FIG. 11 depicts a method 1100 that may be used, for example, for changing an end effector.

The method 1100 (and/or one or more steps thereof) may be carried out or otherwise performed, for example, by at least one processor. The at least one processor may be the same as or similar to the processor(s) 1004 of the computing device 1002 described above. The at least one processor may be part of a robot (such as a robot 1014) or part of a navigation system (such as a navigation system 1018). A processor other than any processor described herein may also be used to execute the method 1100. The at least one processor may perform the method 1100 by executing instructions such as the instructions stored in a memory such as the memory 1006. The instructions may correspond to one or more steps of the method 1100 described below. The instructions may cause the processor to execute one or more algorithms such as algorithm 1020.

The method 1100 comprises aligning a first side of an interface to a first receiver (step 1104). The interface may be the same as or similar to the interface 114 of a connector such as the connector 106. In some embodiments, the interface is a kinematic interface and the connector is a connecting plate. The connector may include the first side and a second side opposite the first side. The interface may include at least one projection such as the at least one projection 138 disposed on each of the first side and the second side. The at least one projection may be receivable by a corresponding recess such as the recess 146 of the first receiver. The first receiver may be the same as or similar to the first receiver 108 of a robot flange such as the robot flange 104. In some embodiments, the first receiver is a first kinematic receiver.

The interface may also include a drape such as the drape 132, 132' to cover a robotic arm such as the robotic arm 112, 1016 so as to create a sterile barrier between the robotic arm and a sterile environment (such as a surgical site). More specifically, a sterile barrier is formed when the drape covers the robot flange and the connector is secured to the robot flange. The connector in such instances is sterile.

In some embodiments, aligning the first side of the interface to the first receiver may comprise aligning each projection of the at least one projection to a corresponding recess of the first receiver. In other embodiments, aligning the first side of the interface to the first receiver may comprise aligning a magnet disposed or otherwise integrated with the connector to a magnet of the opposite polarity disposed or otherwise integrated with the robot flange. In other embodiments, aligning the first side of the interface to the first receiver may comprise aligning a magnet disposed or otherwise integrated with the robot flange to one or more projections of the at least one projection.

The method 1100 also comprises aligning the second side of the interface to a second receiver (step 1108). The second receiver may be the same as or similar to the second receiver 110 of an end effector such as the end effector 102. In some embodiments, the second receiver is a second kinematic receiver. The second receiver may include one or more recesses such as the recess 148 for receiving a corresponding projection disposed on the second side of the interface. In some embodiments, aligning the second side of the interface to the second receiver may comprise aligning each projection of the at least one projection to a corresponding recess of the second receiver.

The method 1100 also comprises locking the end effector to the robot flange (step 1112). The end effector may be locked to the robot flange via a locking assembly such as the locking assembly 116. In some embodiments, locking the end effector comprises coupling the end effector to the robot flange. More specifically, a plurality of projections such as the plurality of projections 118 of the locking assembly may be received by one or more grooves such as the one or more grooves 178 of the robot flange in a snap fit. In some embodiments, the plurality of projections may be disposed between an inner ring such as the inner ring 120 and an outer ring such as the outer ring 122. Locking the end effector may also comprise rotating a nut such as the nut 124 onto the outer ring, which may cause the plurality of projections to press against the groove. The nut may be rotated until the plurality of projections are compressed against the groove, thereby locking the end effector to the robot flange.

The method 1100 also comprises unlocking a first end effector from the robot flange (step 1116). In some embodiments, the end effector comprises a first end effector. Unlocking the first end effector from the robot flange may comprise rotating the nut in an opposite direction of rotation of the nut in step 1112. Rotating the nut in the opposite direction of rotation releases the plurality of projections from compression against the groove, thereby unlocking the first end effector from the robot flange.

The method 1100 also comprises removing the first end effector from the robot flange (step 1120). Removing the first end effector from the robot flange may comprise applying a force to the first end effector to pull the first end effector from the robot flange until the plurality of projections are removed from the corresponding one or more grooves. The force received by the first end effector may cause the inner ring, the outer ring, and the plurality of projections to flex outwardly until the plurality of projections are removed from the one or more grooves. The inner ring, the outer ring, and the plurality of projections may return to an initial position after the plurality of projections are removed from the one or more grooves.

The method 1100 also comprises aligning a second end effector to the robot flange (step 1124). The step 1124 may be the same as or similar to the step 1108 except that the second end effector is a different from the first end effector.

The method 1100 also comprises locking the second end effector to the robot flange (step 1128). The step 1128 may be the same as or similar to the step 1112 except that the second end effector is a different from the first end effector.

It will be appreciated that the steps 1124 and 1128 may be repeated any number of times for any number of end effectors.

It will also be appreciated that a sterile barrier may be maintained between the first end effector and the robot flange and the second end effector and the robot flange when the first end effector is changed for the second end effector. Such sterile barrier provides for interchangeable end effectors that can be changed multiple times through a surgical procedure while maintaining a sterile environment. In some embodiments, the robot flange may include a first electrical connection, the end effector may include a second electrical connection, and the connector may include an electrical connector for transferring power and/or data from the first electrical connection to the second electrical connection. In such embodiments, the sterile barrier may be maintained while transferring power and/or data from the robot flange, through the connector, to the end effector.

The present disclosure encompasses embodiments of the method 1100 that comprise more or fewer steps than those described above, and/or one or more steps that are different than the steps described above.

As noted above, the present disclosure encompasses methods with fewer than all of the steps identified in FIG. 11 (and the corresponding description of the method 1100), as well as methods that include additional steps beyond those identified in FIG. 11 (and the corresponding description of the method 1100). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for changing end effectors comprising:
a flexible connecting plate comprising:
a flexible body including a flexible first surface and a flexible second surface opposite the flexible first surface, wherein the flexible first surface and the flexible second surface are planar; and
a kinematic interface including at least one rigid projection extending from both the flexible first surface and the flexible second surface of the flexible body;
a robot flange having a first kinematic receiver, the first kinematic receiver including at least one recess for receiving a corresponding rigid projection of the at least one rigid projection extending from the flexible first surface of the flexible body;
an end effector having a second kinematic receiver and a locking assembly, the second kinematic receiver including at least one recess for receiving a corresponding rigid projection of the at least one rigid projection on the flexible second surface of the flexible body, the locking assembly configured to releasably secure the end effector to the robot flange; and
a drape connectable to the flexible connecting plate, wherein the locking assembly also secures the drape to the robot flange when the end effector is secured to the robot flange by the locking assembly such that the drape is sandwiched between and contacts the locking assembly and the robot flange.

2. The system of claim 1, wherein the flexible connecting plate is circular.

3. The system of claim 1, wherein the at least one rigid projection comprises at least one sphere.

4. The system of claim 3, wherein the at least one recess of each of the first kinematic receiver and the second kinematic receiver comprises a groove for receiving a corresponding sphere.

5. The system of claim 1, wherein the flexible body comprises plastic, rubber, or silicone.

6. The system of claim 1, wherein the robot flange further comprises a groove, and wherein the locking assembly comprises a first projection.

7. The system of claim 6, wherein the drape is sandwiched between and contacts the groove and the first projection.

8. The system of claim 1, wherein the drape is integrated with the flexible connecting plate.

9. The system of claim 1, wherein the end effector is configured to support a tool.

10. The system of claim 1, wherein the locking assembly comprises a set of projections disposed in a housing of the end effector and a nut.

11. The system of claim 10, wherein the nut includes an angled surface disposed on an inner surface of the nut, the angled surface configured to move and compress each projection in the set of projections against the robot flange when the nut is tightened.

12. A system for changing end effectors comprising:
a flexible connecting plate comprising:
a flexible body comprising a flexible first surface and a flexible second surface, wherein the flexible first surface and the flexible second surface are planar; and
an electrical connector configured to be positioned in an aperture of the flexible body; and a kinematic interface including at least one rigid projection projecting from the flexible first surface and the flexible second surface of the flexible body;

a robot flange having a first kinematic receiver and a first electrical connection, the first kinematic receiver including at least one recess for receiving a corresponding rigid projection of the at least one rigid projection on the flexible first surface of the flexible body; and an end effector having a second kinematic receiver and a second electrical connection, the second kinematic receiver including at least one recess for receiving a corresponding rigid projection of the at least one rigid projection on the flexible second surface of the flexible body;

a drape coupled to the flexible connecting plate; and a locking assembly to secure the end effector to the robot flange, wherein the drape is sandwiched between and contacts the locking assembly and the robot flange when the locking assembly secures the end effector to the robot flange, wherein the electrical connector of the flexible connecting plate is configured to transfer at least one of power and data from the first electrical connection to the second electrical connection.

13. The system of claim 12, wherein the first electrical connection comprises a spring pin connection.

14. The system of claim 12, wherein the robot flange comprises an aperture for supporting the first electrical connection, and the end effector comprises an aperture for supporting the second electrical connection.

15. The system of claim 12, wherein the at least one rigid projection is integrated with the flexible connecting plate.

16. The system of claim 12, wherein the at least one rigid projection is rotatable.

17. The system of claim 12, wherein the robot flange further comprises a groove, wherein the locking assembly comprises a first projection, and wherein the drape is sandwiched between and contacts the groove and the first projection.

18. A system for changing a tool comprising:
a flexible connecting plate comprising:
　a flexible body comprising a flexible first surface and a flexible second surface, wherein the flexible first surface and the flexible second surface are planar; and
　a kinematic interface including at least one rigid projection projecting from the flexible first surface and the flexible second surface of the flexible body, wherein the at least one rigid projection comprises at least one magnet of a first polarity;

a robot flange having a first kinematic receiver and at least one magnet of a second polarity opposite the first polarity, the first kinematic receiver including at least one recess for receiving a corresponding rigid projection of the at least one rigid projection on the flexible first surface of the flexible body;

an end effector configured to support the tool, the end effector having a second kinematic receiver, the second kinematic receiver including at least one recess for receiving a corresponding rigid projection of the at least one rigid projection on the flexible second surface of the flexible body;

a drape coupled to the flexible connecting plate, the drape configured to cover at least the robot flange; and a locking assembly to secure the end effector to the robot flange, wherein the drape is sandwiched between and contacts the locking assembly and the robot flange when the locking assembly secures the end effector to the robot flange, wherein the flexible connecting plate is held in place against the robot flange when the at least one magnet of the first polarity on the flexible first surface of the flexible body is coupled to the at least one magnet of the second polarity.

19. The system of claim 18, wherein the robot flange further comprises a groove, wherein the locking assembly comprises a first projection, and wherein the drape is sandwiched between and contacts the groove and the first projection.

20. The system of claim 18, wherein a sterile barrier is formed when the drape covers the robot flange and the flexible connecting plate is secured to the robot flange.

* * * * *